United States Patent [19]
Iscovich

[11] Patent Number: 5,647,670
[45] Date of Patent: Jul. 15, 1997

[54] BODY FLUID CONTAINMENT BAG

[76] Inventor: Angel Iscovich, 642 Via Trepadora, Santa Barbara, Calif. 93110

[21] Appl. No.: 227,248

[22] Filed: Apr. 13, 1994

[51] Int. Cl.$^6$ .......................... B65D 33/02; B65D 33/25
[52] U.S. Cl. ............................ 383/33; 4/484; 4/267; 383/61; 383/92
[58] Field of Search ........................... 383/33, 34, 92, 383/61; 4/484, 267, 274

[56] References Cited

U.S. PATENT DOCUMENTS

| | | | |
|---|---|---|---|
| 2,142,904 | 1/1939 | Lamarthe | 383/34 |
| 2,943,660 | 7/1960 | Seeger | 383/25 |
| 3,471,871 | 10/1969 | Nociti et al. | 383/61 |
| 3,693,192 | 9/1972 | Knotts | 4/484 |
| 4,792,983 | 12/1988 | Allegre | 383/5 |
| 4,964,739 | 10/1990 | Branson | 383/5 |
| 5,094,707 | 3/1992 | Bruno | 156/244.15 |
| 5,372,428 | 12/1994 | Bruno et al. | 383/5 |

*Primary Examiner*—Stephen P. Garbe
*Attorney, Agent, or Firm*—Michael G. Petit

[57] ABSTRACT

A containment system is described which is useful for the containment of bodily fluids, such as emesis or urine. The fluid containment system is a flexible polymeric bag, preferably polyethylene, of unitary construction having a closed end and a large, normally open, reinforced, "fish mouth" open end through which fluid is introduced into the bag, the reinforced open end having a press and seal closure mechanism. In one embodiment, a strap secures the bag, which is normally in the open or receiving position, around the neck of a person. In another embodiment, straps secure the bag to a belt or belt loops for the collection of urine. In operation, the bag is affixed to the body with a strap which is attached to the (normally open) end of the bag. If the bag is to be used for the collection of emesis, the strap is hung around the neck and dimensioned to position the bag below the chin. The open end of the bag is normally open to receive fluids. The user may, however, push together both ends of the reinforced open end of the bag to further enlarge the opening until the desired shape for the open end is reached. Once set, the open end of the bag will retain its shape. After the emesis occurs the bag can be removed and closed by peeling off a releasable protective strip to expose an inner adhesive strip and grasping the open end of the bag at both ends and pulling taut. The bag is then sealed by sliding the opposed thumb and forefinger along the outside of the bag adjacent to the adhesive strip to insure a liquid-tight seal closure. Self-sealing snaps at the top of the bag insure against accidental opening of the adhesive seal.

2 Claims, 2 Drawing Sheets

BODY FLUID CONTAINMENT BAG

BACKGROUND OF THE INVENTION

1. Field of the Invention

This invention relates to an open form, disposable bag used to contain a material, particularly bodily fluids, and more particularly to a device to contain emesis.

2. Prior Art

During and after emesis, it is important that the body fluid be contained to prevent further exposure of the patient and staff to such fluids as stated in Federal OSHA Requirement 29 CFR section 1910.1030. It is also important that a good sealing device be used on the containment device to prevent further leakage or spillage of the contaminants. Currently, patients are frequently required to vomit into a hard plastic or stainless steel kidney-shaped bowl which only precariously contains contaminants within its small boundaries and also provides no means of sealing contaminants after emesis occurs. Such prior art emesis basins also require that the patient continually hold the bowl. Alternately, a large polymeric type of disposal bag such as a garbage bag has been employed to contain emesis. Such bags can be difficult to maintain in an open position if, for example, one of the user's hands is occupied elsewhere and do not retain their "open mouthed" shape without the intervention of the user. Neither bags nor emesis bowls provide means of sealing off contaminants and require the patient to continually hold the container during use.

As used hereinafter, the term "open form" refers to a container having an open end and a closed end in which the open end is normally held open by means integral with the container while the term "closed form" refers to a bag in which the end through which material is introduced into the container is normally closed and must be opened prior to use. Several devices currently exist that teach the advantages of using a closed form, press-and-seal closure bag to contain body fluids. Representatives of these fluid containment devices are U.S. Pat. Nos. 4,932,791; 3,283,412; 3,797,734, and 4,990,145 incorporated herein by reference. Such containment devices often rely on the cooperative engagement of many separate parts and do not address nor incorporate the necessary components to provide an open form mechanism and a press-and-seal closure in a unitary construction. Prior art devices can also restrict the volume and forcefulness of the emesis and rely fully on the patient or other person for stabilization and control of the device.

Fleury, in U.S. Pat. No. 4,990,145, referenced above, describes an emesis bag with a shield to protect the user's hand from contamination during vomiting. The device comprises a "duck-bill" valve opening in the top of a bag through which bodily fluids are introduced into the bag. The valve is normally in a closed position. It is necessary to open the bag by squeezing the valve in order to introduce fluids therein. Thus, the user must squeeze the bag with at least one hand both prior to and during fluid introduction. Such a container satisfies the description of a "closed form" bag as defined hereinabove.

In an earlier patent, U.S. Pat. No. 3,797,734, Fleury, et al., provide a closed form container for bodily fluids which also requires squeezing to open the bag. A valve prevents the backflow of fluid from the container. No device is currently available that can affix to the patient, be preset and remain in an open form for the hand-free introduction of fluid thereinto, and has a press-and-seal means thereon for proper positive closure.

SUMMARY OF THE INVENTION

The general object of this invention is to provide an open form bag for containment of a material.

It is another object of this invention to provide an open form polyethylene bag which does not require the user to manually open the bag prior to or during the introduction of a material thereinto.

It is still another object to provide a bodily fluid containment system which is of integral construction.

It is yet another object of the invention to provide a bag for material containment which incorporates a positive seal to prevent discharge of material from the bag.

It is another object of the invention to provide a bag of integral construction which is flexible and/or collapsible to facilitate storage.

These and other objects of the invention will soon be apparent as we turn now to a description of the preferred embodiment.

DESCRIPTION OF THE PREFERRED EMBODIMENT

Figure 1:
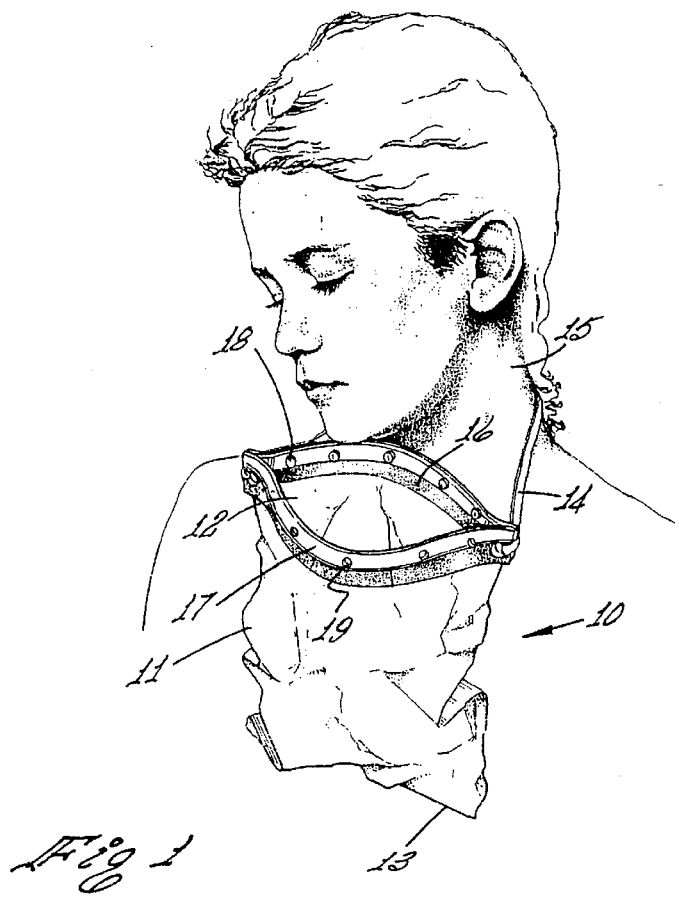
FIG. 1 is a perspective view of a preferred embodiment of the open form bag of the present invention employed for the collection of vomit.

FIG. 1 is a perspective view of a preferred embodiment of the containment bag 10 of the present invention. The bag 10 has a flexible outer wall 11 which extends the length of the containment bag. The bag 10 has an open end 12 and a closed end 13. If the outer wall 11 of the bag is extruded, the closed end 13 may be heat sealed or, alternatively, the outer wall 11 of the bag may be molded with a closed end. The bag 10 preferably has a strap 14 for affixing the bag to the body of a user. The open end 12 is normally in the open position as shown and a material such as body fluids may be introduced into the open end of the bag without manipulation or further intervention by the user. Plastic reinforcing strips, generally indicated at 17 in FIG. 1, are integrally attached to the outer wall 11. The reinforcing strips 17 which maintain the shape of the open end 12 are bowed in a normally outward position as shown. The opposing reinforcing strips 17 preferably have posts with expanded heads 18 and mating holes 19 respectively, which posts and mating holes are opposed to receive one another and sealingly engage. A layer of fluid-impermeable adhesive, generally indicated at 16 is preferably covered by a releasable protective strip of blocking material (not shown). The releasably protective strip can be removed by peeling off prior to sealing and the adhesive provides a positive seal for the open end of the bag after the bag is used.

The bag 10 is preferably made of a thermoplastic or supple polymer such as polyethylene or the like. The bag 10 may be extruded or molded. If the bag is molded, the strips 17 may be conveniently inserted into the mold prior to the injection of the wall material 11. In this way, the reinforcing strip(s) 17 bordering the open end 12 of the bag 10 are integral with the bag and may be sealed with the application of pressure thereto. The strap 14 may be conveniently used to hang the bag around the neck 15 of a patient for the collection of emesis (not shown).

Figure 2:
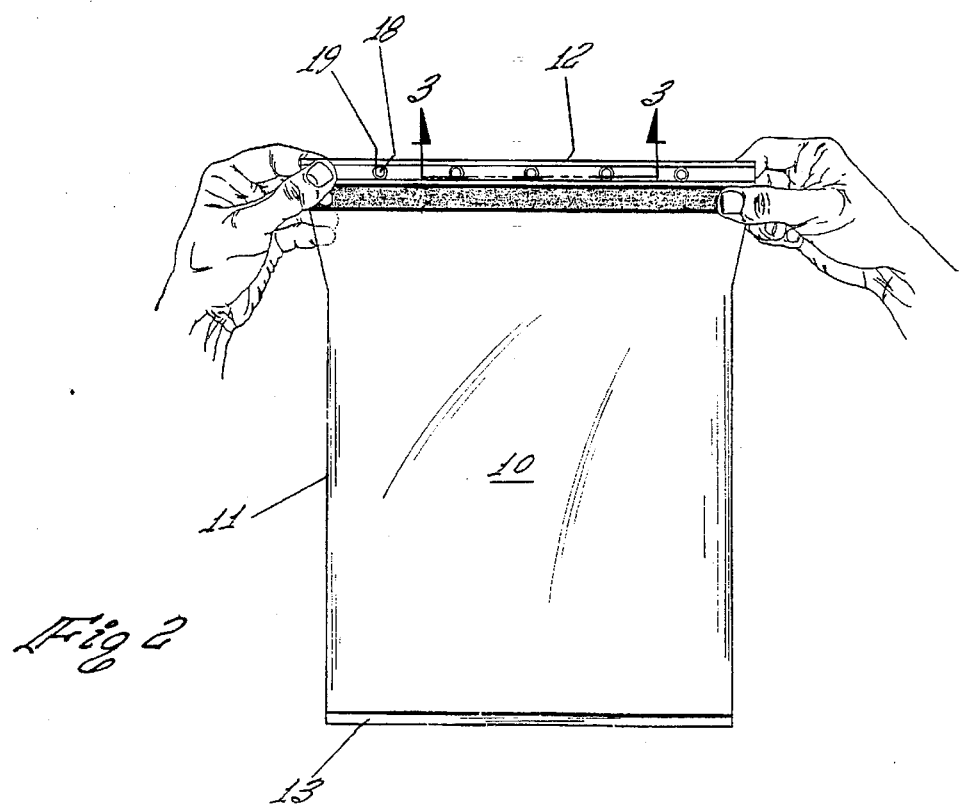
FIG. 2 is a perspective view of the open form bag of the present invention viewed from the front, showing the sealing means.

Turning now to FIG. 2, we see the bag 10 in a position for closing. The contents of the bag (not shown) are prevented from leaving the bag by the closed end 13. The open end 12 of the bag 10 is grasped by the hands and pulled apart. This straightens the flexible strips 17 so that the adhesive layer 16 affixes opposing surfaces of the outer wall 11 of the bag together. Further pressure on the reinforcing strip 17 engages the snaps 18 with their receiving holes 19, firmly locking the open end closed.

Figure 3:
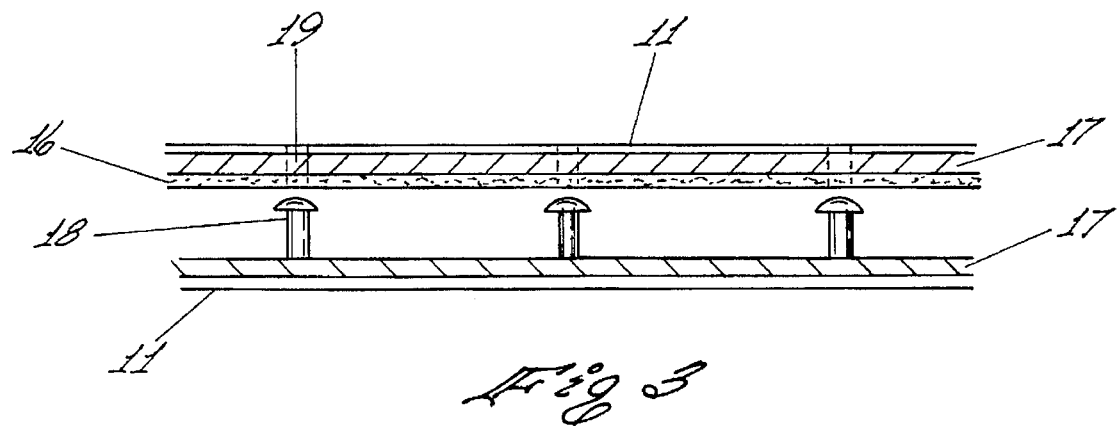
FIG. 3 is a cross-sectional view of the bag of FIG. 2 along section line 3—3 before the bag is sealed.

This is seen more clearly in FIG. 3 which is a cross-sectional view of the bag 10 along section line 3—3 of FIG. 2 immediately prior to closing. It is seen that the adhesive layer 16 is interposed between reinforcing strips 17. The adhesive may also be placed on the wall 11 of the bag immediately above or below the reinforcing strip 17, so that the walls 11 are adhered together. The posts 18 which engage the holes 19 in the opposing side of the open end of the bag have expanded heads which may be barbs or they may be curved fasteners as is shown in the diagram.

Figure 4:
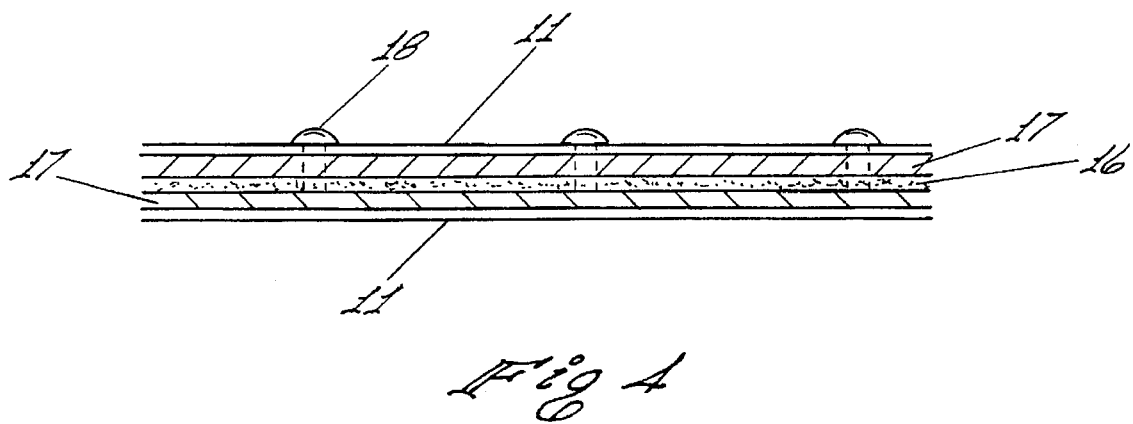
FIG. 4 is the cross-sectional view of FIG. 3 after the open end of the bag has been closed and sealed.

In FIG. 4, the opposing sides of the open end are pressed together. The adhesive layer 16 firmly joins the opposing walls to one another to prevent the escape of fluid material (not shown) from within the bag. The reinforcing strips 17 are prevented from opening by the posts 18 engaging the opposing surface of the bag. Thus, while the adhesive layer 16 provides a leak-proof seal for the open end of the bag, the securing means comprise a post 18 with a mating receiving hole 19 on the opposing wall. Once the post 18 engages or snaps into the hole 19, the bag is prevented from being accidentally pulled open.

It is important to note that at least one of the reinforcing strips 17 adjacent the open end 12 of the bag 10 are arched or formed such that it holds the bag open without the need for user intervention. This unique feature makes it possible for the user to employ his or her hands elsewhere or not at all. Thus, for example, a bag of similar construction may be used for raking leaves into or otherwise placing refuse into where it both hands are required for handling the refuse and there are no hands available for opening the bag. In such an embodiment it would, of course, be preferable that one of the flexible reinforcing strips 17 be straight while the opposing strip is bowed. It is however, intended that the bag be used primarily for the collection of body fluids such as vomit and urine. A pilot, for example, in a small plane may have need to urinate and need both hands for the control of the airplane. Such a bag with a normally open top would provide a convenient container for the urine while enabling the pilot to maintain control of the airplane.

While particular embodiments of the present invention have been illustrated and described, it would be obvious to those skilled in the art that various other changes and modifications can be made without departing from the spirit and scope of the invention. For example, instead of a post and hole type of closure, a zip-lok® type of bead and groove closure may be used as an adjunct to the adhesive sealing means to ensure a positive seal. It is, therefore, intended to cover in the appending claims, all such changes and modifications that are within the scope of this invention.

What I claim is:

1. A collapsible, open form bag for the containment of a body fluid or the like, comprising a tubular member having an open end and a closed end and a flexible outer wall therebetween; said open end further comprising a pair of opposed, flexible, reinforcing strips attached to said flexible outer wall in opposition to one another wherein at least one of said flexible reinforcing strips is arched or bowed to separate said flexible reinforcing strips and create a space therebetween, said space forming an opening in said open end and wherein said open end further comprises fluid-impermeable adhesive means disposed between opposing surfaces of said flexible outer wall, said adhesive means being operable for non-releasably affixing one flexible reinforcing strip to the other.

2. A collapsible, open form bag for the containment of a body fluid or the like, comprising a tubular member having an open end and a closed end and a flexible outer wall therebetween; said open end further comprising a pair of opposed, flexible, reinforcing strips attached to said flexible outer wall in opposition to one another wherein at least one of said flexible reinforcing strips is arched or bowed to separate said flexible reinforcing strips and create a space therebetween, said space forming an opening in said open end and wherein said open end further comprises a plurality of posts having an expanded head on one strip which matingly engage a plurality of holes on the other strip, said posts and holes providing means operable for non-releasably affixing one flexible reinforcing strip to the other.

* * * * *